United States Patent
Miller et al.

[11] Patent Number: 6,021,540
[45] Date of Patent: Feb. 8, 2000

[54] TIP CLEANER FOR OPERATING ROOM INSTRUMENTS

[76] Inventors: Gale W. Miller, 308 Amazon Ave., Cincinnati, Ohio 45220; Charles W. Gay, 5255 Indian Heights Dr., Cincinnati, Ohio 45243

[21] Appl. No.: 08/059,017

[22] Filed: May 5, 1993

Related U.S. Application Data

[63] Continuation of application No. 07/760,358, Sep. 16, 1991, abandoned.

[51] Int. Cl.⁷ ...................................................... A46B 9/02
[52] U.S. Cl. ............................................... 15/160; 15/218
[58] Field of Search ........................ 15/160, 218, 159 A, 15/DIG. 5, 244.1

[56] References Cited

U.S. PATENT DOCUMENTS

| | | | |
|---|---|---|---|
| D. 236,564 | 9/1975 | Kaufman | 15/114 X |
| D. 242,668 | 12/1976 | Kaufman | 15/114 X |
| 414,145 | 10/1889 | Cyrenius | 15/161 |
| 1,437,794 | 12/1922 | Cleveland | 15/160 X |
| 2,128,011 | 8/1938 | Morgan | 15/164 |
| 2,174,214 | 9/1939 | Quinn | 15/160 |
| 2,250,112 | 7/1941 | Larson | 15/159 A |
| 3,093,855 | 6/1963 | Stevens | 15/160 |
| 3,107,665 | 10/1963 | Nordgren | 15/159 A |
| 3,214,777 | 11/1965 | Kutik | 15/159 A |
| 3,556,667 | 1/1971 | Kaufman | 15/114 X |
| 3,815,923 | 6/1974 | Goduto | 15/159 A |
| 4,087,878 | 5/1978 | Grieshaber et al. | 15/111 |
| 4,384,384 | 5/1983 | Trojohn | 15/160 X |
| 4,420,853 | 12/1983 | Gilman et al. | 15/111 |
| 4,807,652 | 2/1989 | Bachrach | 15/159 A |
| 4,853,041 | 8/1989 | Clardy | 15/160 |
| 4,890,348 | 1/1990 | Racioppi | 15/160 |
| 4,945,598 | 8/1990 | Racioppi | 15/160 |

FOREIGN PATENT DOCUMENTS

| | | |
|---|---|---|
| 583957 | 9/1959 | Canada . |
| 483333 | 11/1935 | United Kingdom . |
| 515233 | 11/1939 | United Kingdom . |

*Primary Examiner*—Patrick Brinson
*Attorney, Agent, or Firm*—Wood, Herron & Evans, L.L.P.

[57] ABSTRACT

A cleaning device for surgical implements comprising a base and upstanding bristles, including at least one sharp vertical edge and a flat top. The bristles of one section are short and rigid, the bristles of the second section are long are relatively flexible, and the bristles of an intermediate section vary in length from short to long with a substantial portion of the intermediate bristles being relatively rigid so that a suction tube can be cleaned by pressing it downwardly over the bristles. The base carries a resilient pad and a securing member such as a double-faced adhesive tape for mounting the unit upon a support surface.

16 Claims, 1 Drawing Sheet

TIP CLEANER FOR OPERATING ROOM INSTRUMENTS

This application is a continuation of application Ser. No. 07/760,358, filed Sep. 16, 1991 now abandoned.

BACKGROUND OF THE INVENTION

The present invention relates to devices for cleaning operating room instruments. During the course of performing a surgical procedure, many of the instruments used by the surgeon, such as electrocautery tips, suction tips, bipolar tips, become coated with coagulum, particles of tissue and the like. Also, the bores of the suction tips tend to become clogged due to the accumulation of material. In practice, the surgeon in most instances hands an instrument which has accumulated debris or is clogged to an assistant who cleans the instrument with a gauze sheet or the like and returns it to the surgeon. In some instances, a surgeon is able to clean some of the instruments by rubbing them against a sandpaper type pad, which is secured to the operating table, a drape or some other accessible area.

It has also been proposed in U.S. Pat. No. 4,087,878 to provide a device for cleaning surgical knives in the form of a setose member having upstanding setae mounted within a housing having elongated slots. This cleaning member is used by surgeons to clean knives by inserting the knives through the slot and rubbing it against the setae.

Each of these methods for cleaning operating room instruments is subject to one or more serious drawbacks. In the first place, in a procedure in which the surgeon is required to hand off the operating instrument to an assistant for cleaning, extra time is required as opposed to an arrangement in which the surgeon can quickly clean his own instruments. Moreover, when instruments are interchanged between a surgeon and an assistant, there is always a possibility that the assistant will return a different instrument to a surgeon, for example, a suction tip of a different size. This can have quite deleterious results.

Another difficulty with cleaning devices such as a sandpaper pad or the setose member mounted within a slotted housing is that these devices are not effective for cleaning out the interior of suction tubes.

SUMMARY OF THE PRESENT INVENTION

It is the principal object of the present invention to provide a cleaning device for surgical instruments which enables a surgeon, using only one hand, to rapidly and efficiently clean all types of instruments, including suction tubes, without handing them off to an assistant.

The present invention is predicated in part upon the concept of providing a cleaning device comprising a plurality of upstanding bristles at least some of which are relatively rigid, the bristles being mounted upon a base member which can be secured in any suitable manner, such as by adhesive backing, to an operating room drape, or a surgeon's gown or wrist, or indeed to any other convenient and accessible place. The bristles are dimensioned and spaced so that any suction tube within a relatively wide range of sizes can be moved downwardly over the bristles and one or more bristles will enter the tube to dislodge materials which are then withdrawn by suction.

The present invention is further predicated upon the concept of providing a cleaning unit having several sections with the bristles within each section being of different heights and having markedly different characteristics. In one section the bristles are short, stubby and rigid. In another section the bristles are relatively long and flexible, while in a third or intermediate section the bristles vary in height from the shortest bristles to the longest bristles. These intermediate bristles are sufficiently rigid so as to remain upright and to penetrate a suction tube which is brought down over the bristles which enter the tube and free any coagulum or the like which might clog the tube.

The present invention contemplates the use of bristles which provide an enhanced scraping or cleaning action for effectively removing coagulum and other debris from the surgical instruments. More particularly, in a preferred form, the bristles have one or more vertical sharp edges and flat tops which facilitate the scraping action of the bristles. Bristles which are not circular in cross-section are further advantageous since they allow air to pass around the bristles while inside a suction tube, thus enhancing the cleaning action.

In use, the surgeon engages the instrument to be cleaned with the group of bristles most effective to perform the necessary cleaning operation. For example, coagulum can be removed from an electrocautery tip by dragging and/or pushing the tip across the short, rigid bristle section of the cleaner. The exterior of suction tips can be cleaned by rotating the tube through bristles in the intermediate section or long section. The interior of the suction tube is cleaned by moving the tube vertically up and down over either the intermediate or long bristles which enter the tube to dislodge any coagulum or the like which is, in turn, withdrawn from the tube by suction. The exterior of suction tips and other instruments can also be cleaned by drawing the instrument through the long flexible bristles, preferably while pressing the instrument down into the bristle mass.

One advantage of the present cleaning device is that it enables a surgeon using only one hand to clean the instruments he is using without handing the instruments off to an assistant.

Another advantage of the present invention is that the instruments are effectively cleaned and left in an uncontaminated condition. More particularly, a substantial portion of the debris, coagulum or the like adhering to the instrument, is not only scraped from the instrument by the bristles, but remains entrapped by the bristles and does not remain attached to the instrument. Furthermore, there is no extraneous contaminating material, such as sandpaper type grit or the like, or scraped off coagulum debris which might be picked up by the surgical instruments.

A further advantage of the present invention is that the cleaning device can be mounted in any location which is preferred by the surgeon. For example, the device may be mounted upon the drape, attached to the surgeon's gown, attached to the surgeon's wrist by means of a strap or the like, or secured to a portion of the operating table. The surgeon is thus able to perform the operation at hand without wasting time transferring instruments to an attendant. He is able to exert maximum concentration upon the operating procedure since he is freed from the necessity of interacting with an attendant in order to clean the instruments in use.

A still further advantage of the present cleaning device is that it is simple and inexpensive. The device is disposable and can be discarded at the end of an operation without requiring anyone to come into contact with the coagulum and other debris entrapped in the bristles.

These and other objects and advantages of the present invention will be more readily apparent from a further consideration of the following detailed description of the drawings illustrating a preferred embodiment of the invention.

DESCRIPTION OF A PREFERRED EMBODIMENT

Figure 1:
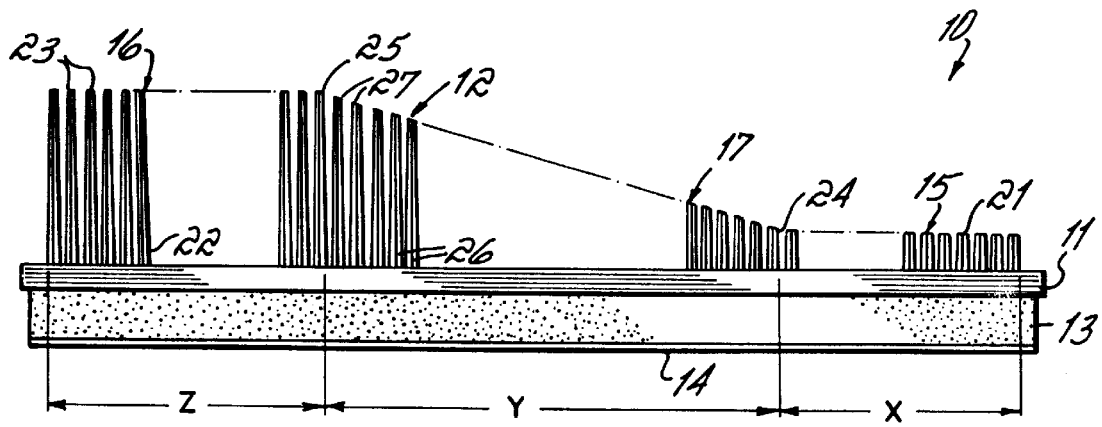
FIG. 1 is an elevational view of a preferred form of tip cleaner constructed in accordance with the principles of the present invention.

A preferred form of tip cleaner 10 constructed in accordance with the present invention is illustrated in FIG. 1. As there shown the tip cleaner comprises a base section 11 having a plurality of integral bristles 12 extending upwardly therefrom. In the preferred embodiment, base and bristles are formed of a suitable plastic material such as ethylene vinyl acetate. The base is preferably rectangular in configuration. One suitable size of base is 3" in length by 2" in width and approximately 0.08" in thickness.

Figure 2:
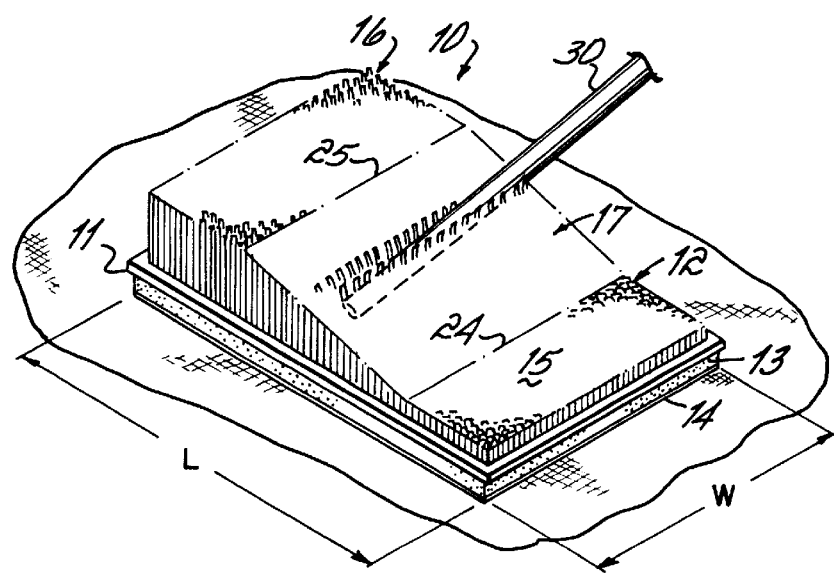
FIG. 2 is a perspective view of the tip cleaner of FIG. 1 illustrating the manner in which the exterior of a suction tip is cleaned.

In a preferred embodiment, a resilient pad 13 formed of a suitable foam material, such as polyurethane foam, is adhered to the bottom surface of the base 11. This pad may be of any suitable thickness, for example, ¼". The lower surface of the pad carries means for securing the tip cleaner unit 10 to a drape, operating table or other surface, such as for example, a surgeon's gown (FIG. 2). The pad can alternatively be mounted to a wristband to be worn by a surgeon. One suitable form of attaching means 14 is double-faced adhesive tape. One surface of the tape is adhered to the foam pad 13 while the exposed surface of the tape is adapted to be adhered to the selected support surface.

Figure 3:
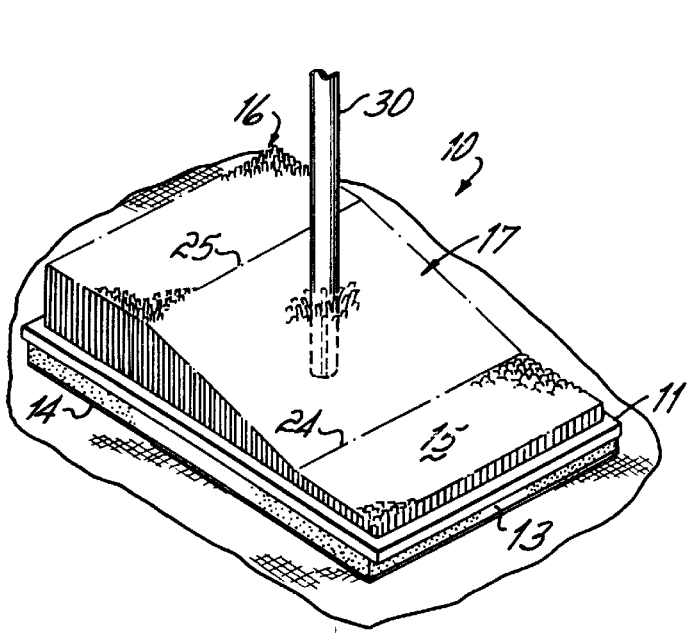
FIG. 3 is a perspective view of the tip cleaner of FIG. 1 showing the cleaning of the interior of a suction tip.

As shown in FIGS. 1, 2 and 3, the bristles 12 are formed of different heights to define a short bristle section 15, long bristle section 16, and an intermediate length bristle section 17. In a preferred embodiment of the invention, the length X of the short bristle section 15 is approximately ¾" while the length of the intermediate section Y is approximately 1⅜" and the length of the long section Z is approximately ⅞". Obviously, the relative lengths of these sections can be varied if desired.

Figure 4:
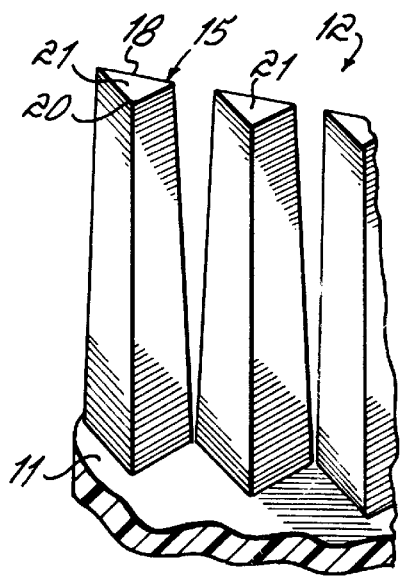
FIG. 4 is a greatly enlarged perspective view of the short bristles forming part of the cleaner.

The configuration of the individual bristles is best illustrated in FIGS. 1 and 4. It is to be understood that FIG. 4 illustrates the bristles 12 forming part of the short bristle section 15. However, in a preferred embodiment the lower portions of the bristles forming long bristle section 16 and intermediate length bristle section 17 are substantially identical with the bristles of the short section.

As shown in FIG. 4, each individual bristle 12 includes at least one vertical edge 20. Most preferably, the bristle is of triangular cross-section with a base wall 18 being approximately 0.032" in length and the altitude from that base wall to the opposite apex of vertical edge 20 being approximately 0.025". The height of the bristles in the short section is approximately 0.1". The bristles are preferably spaced so that the center-to-center distance of the bristles across the width W of the base is approximately 1/16". The center-to-center distance of the bristles along the length L of the base is approximately 0.050". The tops 21 of the bristles are substantially flat and horizontal as illustrated in FIG. 4. As a consequence of their configuration and dimensions, the bristles 12 of short bristle section 15 are quite rigid. The bristles extend vertically from the base and are not angularly displaced any appreciable amount when they are engaged by a surgical instrument.

The bristles of long bristle section 16 are preferably about ½" in height. The lower portions 22 of these bristles are substantially identical with the bristles 12 of section 15. The long bristles of section 16 taper from their lowermost portions 22 to their ends 23. Preferably, this taper is as slight as possible to accommodate the molding operation. The bristles preferably are of triangular configuration all of the way from their juncture with base 11 to the tips 23. The tips 23 of the long bristles are preferably flat and horizontal. The characteristics of the long bristles of section 16 are such that the bristles extend generally upwardly from the base 11. However, the bristles may bend slightly and are readily displaced in any direction by engagement with a surgical instrument. These bristles feel relatively soft to the touch as opposed to the bristles of section 15, which feel generally like a rough rigid surface.

The bristles of intermediate section 17 are of intermediate heights between the heights of long bristles 16 and short bristles 15. In a preferred embodiment, the bristles of intermediate section 17 vary gradually in height from 0.1" at the juncture 24 of sections 15 and 17 to 0.5" at the juncture 25 of sections 16 and 17. The bristles of intermediate section 17 of lower portions 26 are substantially identical with the short bristles of section 15. The bristles of the intermediate section taper upwardly from lower section 26 to their tips 27 with the cross-section of the bristles remaining triangular. The upward taper of the bristles of intermediate section 17 is preferably as small as possible to accommodate the molding of these bristles. Again, the tips 27 of the bristles of intermediate section 17 are preferably flat and substantially horizontal. In the preferred embodiment, a substantial portion of the bristles of intermediate section 17 are slightly more flexible than the bristles of short section 15, but are appreciably more rigid than the bristles of long section 16. The bristles of intermediate section 17 preferably remain upstanding and parallel to one another after a surgical instrument has been pressed against the bristles and removed.

In use, a tip cleaner unit 10 which has been sterilized is removed from its sterile package. Using the double-faced tape 14 or other mounting means the tip cleaner unit is secured in any convenient location, such as on the drape. Alternatively, the tip cleaner unit can be carried by a band secured to the surgeon's wrist. As a surgeon proceeds with the operation, the unit 10 can be used by the surgeon to clean various types of operating instruments, such as electrocautery tips, suction tips, bipolar tips, laser fibers, or burrs. For example, coagulum can be cleaned off of an electrocautery tip by rubbing it against the tips of the short bristles of section 15. The short stubby bristles of this section with their flat tops and sharp edges have a very effective shearing action which scrapes the electrocautery tip clean as it is rubbed back and forth across the bristle tips of this section. The debris which is scraped off the tip is trapped and held between the bristles of this section.

A second type of instrument which can be cleaned using the present tip cleaner unit is a suction tip 30. These tips have various size tubular bores, for example, from 1/16" to ¼". Suction tips 30 tend to accumulate debris both on the outer surface of the tip and within the bore. The exterior of the suction tip 30 can be cleaned by dragging the tip through either the long bristles of section 17 of the unit or the portion of intermediate section close to the long bristles (FIG. 2). The vertical edges of the bristles increase the effectiveness of the scraping action so that all of the debris is removed from the outer surface of the tip. The interior of the suction tip is quickly and easily cleared or cleaned out by repeatedly and rapidly moving the tip up and down, vertically over the bristles of intermediate section 17 or long section 16 (FIG. 3). These bristles are relatively rigid and extend upwardly into the tip opening. The bristles thus push the obstructing material free from the tip walls so that it is carried away into the suction line.

Another type of instrument which can be cleaned using the present unit is a bipolar cautery tip. The coagulum which accumulates on the interior surface of these tips can be cleaned off by pulling the tips through the bristles of the intermediate section 17, preferably with a slight squeezing motion. The coagulum is scraped from the tips with an enhanced shearing action due to the sharp edges of the bristles, and is trapped or captured between the bristles.

The long bristle section 16 of the cleaner unit can be used to clean debris off of suction tips by dragging the tips through the long bristles while pressing the tip downwardly into the bristles. This motion can be repeated and accompanied by a rotating motion to enhance the cleaning action. In addition to the above instruments, the cleaner unit can be utilized to clean off laser fibers and burrs by pulling them through the long bristles of section 16 of the unit.

At the conclusion of the operation, the tip cleaner 10 is stripped from its supporting surface and disposed of. This can be accomplished without requiring the user to contact the material retained between the bristles.

From the foregoing disclosure of the principles of the present invention and the above description of a preferred embodiment, those skilled in the art will readily comprehend various modifications to which the invention is susceptible. Thus, it is contemplated that the overall dimensions of the cleaner unit 10 as well as the dimensions of the individual fibers can be varied. Furthermore, it is contemplated that the unit can be formed from a suitable plastic material other than ethylene vinyl acetate, for example, styrene, nylon or the like, if desired. Also, alternate attachment means, such as velcro tape or the like, can be substituted for the double-sided tape shown in FIG. 1.

Accordingly, we desire to be limited only by the scope of the following claims.

Having described our invention, we claim:

1. A cleaning device for surgical instruments comprising:
   a base,
   a plurality of bristles each having a longitudinal axis extending outwardly from said base, said bristles forming first, second and third sections,
   each of said sections comprising a plurality of rows of bristles, each of said rows comprising a plurality of bristles,
   each of said bristles being of a non-circular cross-section and having a longitudinal axis, each of said bristles further having at least one edge extending parallel to said axis,
   the bristles of said first section being relatively long and flexible,
   the bristles of said second section being of a height substantially less than half the height of the bristles of said first section, the bristles of said second section being rigid,
   the height of the bristles of said third section being intermediate the height of the bristles of said first and second sections,
   the bristles of said first section and a substantial number of bristles of said third section being sufficiently rigid that when a section tube is forced downwardly over said bristles, the bristles enter said suction tube and dislodge any material clogging said tube,
   and attaching means secured to said base for releasably attaching said base to a surface.

2. The cleaning device of claim 1 in which the bristles of said first section are of the order of ½" in height and the bristles of said second section are of the order of ¹⁄₁₀" in height.

3. The cleaning device of claim 1 in which each of said bristles of triangular cross-section.

4. The cleaning device of claim 3 in which each of said bristles has a flat top.

5. The cleaning device of claim 3 in which the maximum transverse dimension of said bristles is about 0.03".

6. The cleaning device of claim 5 in which the center-to-center spacing of said bristles is about 0.05".

7. A cleaning device for surgical instruments comprising:
   a base,
   a plurality of bristles each having a longitudinal axis extending outwardly from said base, said bristles forming first and second sections,
   each of said sections comprising a multiplicity of rows of bristles, each of said rows comprising a multiplicity of bristles,
   each of said bristles being of a non-circular cross-section and having a longitudinal axis, each of said bristles further having at least one edge extending parallel to said axis,
   the bristles of said first section being relatively long and flexible,
   the bristles of said second section being of a height of the order of ¹⁄₁₀" and being substantially less than half the height of the bristles of said first section, the bristles of said second section being rigid,
   the bristles of said first section being sufficiently rigid that when a suction tube is forced downwardly over said bristles the bristles enter said suction tube and dislodge any material clogging said tube, and
   attaching means secured to said base for releasably attaching said base to a surface.

8. The cleaning device of claim 7 in which each of said sections comprises several hundred bristles.

9. The cleaning device of claim 7 in which each of said sections is at least one square inch in area.

10. The cleaning device of claim 7 in which each of said bristles of triangular cross-section.

11. The cleaning device of claim 7 in which each of said bristles has a flat top.

12. A cleaning device for surgical instruments comprising:
   a base,
   a plurality of bristles each having a longitudinal axis extending outwardly from said base, said bristles forming first and second sections,
   each of said sections comprising a multiplicity of rows of bristles, each of said rows comprising a multiplicity of bristles,
   each of said bristles being of a non-circular cross-section and having a longitudinal axis, each of said bristles further having at least one edge extending parallel to said axis,
   the bristles of said first section being relatively long and flexible, the bristles of said second section being of a height of the order of 1/10" and being rigid, the bristles of said first section varying in height, some of said bristles being several times the height of the bristles of said second section and being sufficiently rigid that when a suction tube is forced downwardly over said bristles the bristles enter said suction tube and dislodge any material clogging said tube, and attaching means secured to said base for releasably attaching said base to a surface.

13. The cleaning device of claim 12 in which each of said sections comprises several hundred bristles.

14. The cleaning device of claim 12 in which each of said sections is at least one square inch in area.

15. The cleaning device of claim 12 in which each of said bristles of triangular cross-section.

16. The cleaning device of claim 12 in which each of said bristles has a flat top.

* * * * *

UNITED STATES PATENT AND TRADEMARK OFFICE
CERTIFICATE OF CORRECTION

PATENT NO. : 6,021,540
DATED : February 8, 2000
INVENTOR(S) : Gale W. Miller et al.

It is certified that error appears in the above-identified patent and that said Letters Patent is hereby corrected as shown below:

Title page,
ABSTRACT, item [57], line 4, change "are long are" to -- are long and --.

Column 6, claim 1,
Line 3, change "section" to -- suction --.

Column 6, claim 3,
Line 13, change "of" to -- has a --.

Column 6, claim 10,
Line 49, change "of" to -- has a --.

Column 8, claim 15,
Line 6, change "of" to -- has a --.

Signed and Sealed this

Second Day of April, 2002

*Attest:*

JAMES E. ROGAN
*Attesting Officer*     *Director of the United States Patent and Trademark Office*